United States Patent [19]

Panster et al.

[11] Patent Number: 5,340,895
[45] Date of Patent: Aug. 23, 1994

[54] FORMED, POLYMERIC TRANSITION-METAL COMPLEX CATALYSTS WITH ORGANOSILOXANE DIPHENYLPHOSPHINE LIGANDS

[75] Inventors: Peter Panster, Rodenbach; Robert Gradl, Alzenau; Peter Kleinschmit, Hanau, all of Fed. Rep. of Germany

[73] Assignee: Degussa Aktiengesellschaft, Frankfurt, Fed. Rep. of Germany

[21] Appl. No.: 43,604

[22] Filed: Apr. 5, 1993

Related U.S. Application Data

[63] Continuation of Ser. No. 786,796, Nov. 1, 1991, abandoned.

[30] Foreign Application Priority Data

Nov. 3, 1990 [DE] Fed. Rep. of Germany ....... 4035033

[51] Int. Cl.$^5$ .................. C08G 77/26; C08G 77/30; C08G 77/06
[52] U.S. Cl. .......................... 528/9; 528/39; 528/38; 528/30
[58] Field of Search ............ 528/9, 39, 38, 30

[56] References Cited

U.S. PATENT DOCUMENTS

| | | | |
|---|---|---|---|
| 3,097,852 | 9/1975 | Oswald et al. | 260/448.2 N |
| 4,067,820 | 1/1978 | Wagner et al. | 252/426 |
| 4,276,195 | 6/1981 | Verkade | 252/431 P |
| 4,424,332 | 1/1984 | Panster et al. | 528/30 |
| 4,442,040 | 4/1984 | Panster et al. | 260/429 R |
| 4,482,752 | 10/1984 | Mitchell et al. | 585/670 |
| 4,520,122 | 5/1985 | Arena | 502/152 |
| 4,578,496 | 3/1986 | Panster et al. | 556/479 |
| 4,647,679 | 3/1987 | Panster et al. | 556/9 |
| 4,657,884 | 4/1987 | Luft et al. | 502/161 |
| 4,845,163 | 7/1989 | Panster et al. | 525/475 |
| 4,895,817 | 1/1990 | Ogata | 502/158 |
| 4,954,599 | 9/1990 | Panster et al. | 528/38 |
| 4,999,413 | 3/1991 | Panster et al. | 528/30 |
| 5,093,451 | 3/1992 | Panster et al. | 528/9 |
| 5,094,831 | 3/1992 | Klockner et al. | 423/342 |

FOREIGN PATENT DOCUMENTS

| | | |
|---|---|---|
| 3029599 | 2/1982 | Fed. Rep. of Germany . |
| 0072435 | 2/1983 | United Kingdom . |
| 0151991 | 8/1985 | United Kingdom . |
| 0327795 | 8/1989 | United Kingdom . |

OTHER PUBLICATIONS

*The Bantam New College German & English Dictionary* 1981, p. 331, p. 285.

Grubbs, R. H., "Hybrid-phase catalysts", *Chemtech* (Aug. 1977), pp. 512–518.

Ejike, E. N. et al., "Insoluble Poly(akylarylphosphine) siloxanes and their application as supports for catalytic transition-complexes", *Journal of Applied Polymer Science* (1989), vol. 38, pp. 271–280.

Parish, R. V., et al., "Insoluble ligands and their applications. II. Polysiloxane-phosphine ligands, their complexes, and hydrogenation catalysts", *Journal of Organometallic Chemistry* (1989), vol. 369 pp. 17–28.

*Primary Examiner*—John C. Bleutge
*Assistant Examiner*—Margaret W. Glass
*Attorney, Agent, or Firm*—Beveridge, DeGrandi, Weilacher & Young

[57] ABSTRACT

Formed spherical polymeric complexes of metals of the 8th subgroup of the periodic system with ligands of an organosiloxane copolycondensate optionally cross-linked by means of cross-linking agents containing Si, Ti, Zr and/or Al (statistical, block-shaped or mixed). This copolycondensate consists of the units

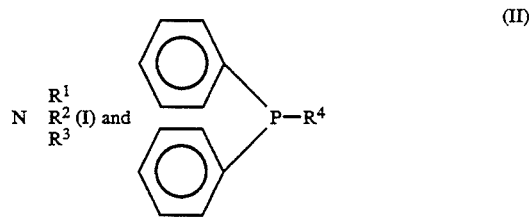

in which R$^1$–R$^4$=R$^5$–Si (Abstract continued on next page.)

O—
O—
O— in which $R^5$ = alkylene with $C_1$–$C_{10}$ directly bound to P or N, cycloalkylene with $C_5$–$C_8$ or

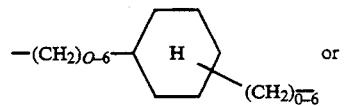

or

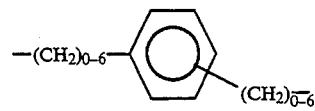

The ratio between the number of moles of units (II) and the number of moles of bound metal atoms is 1:1 to 1.000 to 1 and the ratio between units (I) and (II) is preferably 10:90 to 95:5 mole %.

The polymeric complex compounds are present macroscopically as spherical particles with a diameter of 0.01. to 3.0 mm, a BET surface of >0 to 1000 m²/g, a specific pore volume of 0.01 to 6.5 ml/g, and a bulk density of 50 to 1000 g/l.

Several methods of preparing the substance of the invention with special posttreatment stages and the use of the polymeric metal complexes as catalysts in organic chemistry are disclosed.

21 Claims, No Drawings

FORMED, POLYMERIC TRANSITION-METAL COMPLEX CATALYSTS WITH ORGANOSILOXANE DIPHENYLPHOSPHINE LIGANDS

This application is a continuation of application Ser. No. 07/786,796, filed Nov. 1, 1991, now abandoned.

BACKGROUND OF THE INVENTION

The subject matter of the present invention concerns polymeric transition-metal complex catalysts with organosiloxane diphenylphosphine ligands which are present as formed copolycondensates. The formed, polymeric, insoluble complex compounds of Fe, Co, Ni, Ru, Rh, Pd, Os, Ir and/or Pt exhibit the engineering and application-technology advantages of a macroscopic spherical form and have the physical properties necessary for use as heterogenized complex catalysts. Methods are also described according to which the novel products can be prepared not only in the spherical size desired for the particular use but also with the suitable physical properties. In addition, the use of these polymeric catalysts is described.

Homogeneous catalysts that are used exhibit without exception a higher activity and selectivity than comparable heterogeneous catalysts. However, rather significant engineering problems generally occur in the use of these catalysts in connection with their separation of the formed product from solvent present and with their recycling. Moreover, the recovery of the expensive noble-metal component from the residues of the reaction mixture is expensive and can normally only be carried out with rather significant metal losses.

Another disadvantage of homogeneous catalysts that are used is the frequently rather short residence time caused by the formation of catalytically inactive species.

In order to circumvent the above described disadvantages of so-called homogeneous catalysts, there has already been followed for some time worldwide the development of so-called heterogenized homogeneous catalysts (heterogenized catalysts) in which the homogeneous catalyst normally used is bound to a solid carrier.

The state of the art in this area of catalysis has already been summarized in appropriate survey literature, e.g. by R. H. Grubbs in CHEMTECH, Aug. 1977, p. 512; by F. R. Hartley in "Catalysis by Metal Complexes", D. Reidel Publ Co., 1985; or also by Yu. I. Yermakov et al. in "Catalysis by Supported Complexes", Elsevier Scientific Publ. Co., 1981.

However, up to the present, for a number of reasons the organic and inorganic polymer systems used as carrier materials have met the desired requirements only to a very limited extent. In the case of organic polymer carriers, the physical and mechanical properties, in particular, as well as the too low chemical stability, represent disadvantages; whereas inorganic polymer carriers such as silica gel have the disadvantage of a functionality which is too low and, in addition, insufficiently defined.

Novel, heterogenized metal complex catalysts which do not exhibit the above described disadvantages of the previous systems were recently developed, as is described in German patent 30 29 599. The matrix of these polysiloxane catalysts has practically the advantages of an inorganic polymer carrier and, in addition, can be produced approximately on a made to order basis, e.g. as regards the important aspects, namely, that the metal : ligand ratio can be varied or that so-called cross-linking agents can be integrated into the matrix or that a control of the catalytic central density and distribution is possible. Compared to systems with purely inorganic carriers, these organopolysiloxane polymers display in particular the advantages of a higher metal concentration, of simpler preparative accessibility, and of greater stability vis-à-vis chemical degradation.

In particular, the polymeric metal phosphine complexes mentioned in German patent 30 29 599, which generally exhibit very good catalytic properties, were synthesized according to this concept. However, these heterogenized complex catalysts have the disadvantage that they could previously be prepared only in a relatively undefined macroscopic shape and not in the spherical form advantageous in application technology with the desired physical and morphological properties.

SUMMARY OF THE INVENTION

An object of the present invention is to solve the problem of preparing heterogenized transition-metal complexes with organosiloxane diphenylphosphine ligands in spherical form, and with the desired physical properties, in a reproducible manner.

DETAILED DESCRIPTION OF THE INVENTION

Subject matter of the invention is constituted by formed spherically shaped, polymeric metal complexes of iron, cobalt, nickel, ruthenium, rhodium, palladium, osmium, iridium and/or platinum. They are characterized in that the ligand consists of a formed organosiloxane copolycondensate consisting of units of the formula

and of units of the formula

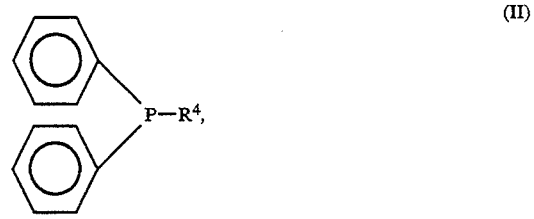

wherein the central metal atom is coordinatively bound via the strongly bonding phosphorus atoms of tile phosphine units (II) or, additionally, also via the more weakly bonding nitrogen atoms of tile amine units (I) , $R^2$ to $R^4$ are the same or different and signify a group of the formula

in which $R^5$ is bound directly to the phosphorus atom or to the nitrogen atom and represents a linear or branched alkylene group with 1 to 10 C atoms, a cycloalkylene group with 5 to 8 C atoms or a unit of the general formula

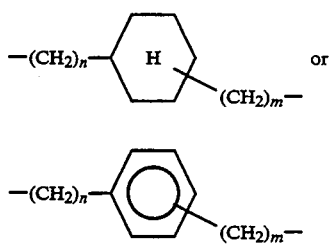

in which "n" and "m" are a number from 0 to 6, that "n" indicates the number of methylene groups bound to N or bound to P and "m" the number of methylene groups bound to Si, $R^1$ represents a group of formula (III) or stands for H, $CH_3$, $C_2H_5$, $C_3H_7$, where the free valences of the oxygen atoms bound to the Si atom are saturated (as in silica skeletons) by silicon atoms of further groups of formula (III) and/or via the metal atoms in one or several cross-linking bridge members (IV)

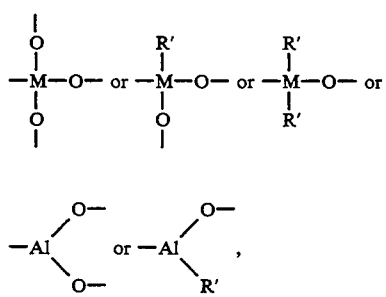

M is an Si, Ti or Zr atom and R' is a linear or branched alkyl group with 1 to 5 C atoms or a phenyl group,
and the ratio of the silicon atoms from the groups of formula (III) to the metal atoms in the cross-linking bridge members (IV) is 1:0 to 1:20 and the molar ratio of phosphine units (II) to complexed metal units is 1:1 to 1000:1, preferably 1:1 to 100:1,
and where the polymeric complex catalysts are present macroscopically as spherical particles with a diameter of 0.01 to 3.0 mm, preferably 0.05 to 2.0 mm, with a BET specific surface of >0 to 1000 $m^2/g$, preferably >0 to 700 $m^2/g$, and with a specific pore volume of 0.01 to 6.5 ml/g, and with a bulk density of 50 to 1000 g/l, preferably 100 to 700 g/l.

It proved to be especially advantageous, both as concerns the preparation and the physical properties as well as in regard to the catalytic properties of the heterogenized complex catalysts as polymer ligand system, to use a copolycondensate with amine groups and phosphine groups. Certain copolycondensates have been described in German patent application P 39 25 359.7.

The ratio of units according to formula (I) to units according to formula (II) can vary greatly and can be within the limits of 10 : 90 to 95 : 5 mole %. No problems with the morphological, physical and chemical properties of the polymeric complex catalysts of the invention occur thereby.

A particular embodiment of the invention provides that $R^1$ to $R^4$ are a group of the general formula (III) and are identical or different.

The ratio to be selected in practice depends primarily on the complex to be prepared as well as on the intended area of use and the chemical and physical properties required for it, e.g. on whether a high metal concentration or a high density of the phosphine component or amine component as regards catalytic properties or metal adhesion is required or not.

The monomeric structural elements of the formed polymer ligand system are basically known compounds, e.g. of the formulas $N((CH_2)_3Si(OC_2H_5)_3)_3$ $N((CH_2)_{10}Si(OH_3)_3)_3$ $(C_6H_5)_2P(CH_2)_3Si(OCH_3)_3$ $Si(OC_2H_5)_4$ $(H_3C)_2Si(OC_2H_5)_2$ $Ti(OC_3H_7)_4$.

The composition of the polymer units obtainable from them can be described by the formulas $N((CH_2)_3SiO_{3/2})_3$ $N((CH_2)_{10}SiO_{3/2})_3$ $(C_6H_5)_2P(CH_2)_3SiO_{3/2}$ $SiO_{4/2}$ $(H_3C)_2SiO_{2/2}$ $TiO_{4/2}$.

The spherically shaped copolycondensates can be present even in the case of the same chemical composition in completely different form as so-called statistical copolycondensates ("random copolycondensates") or as block copolycondensates or also as so-called mixed copolycondensates; such terms are well known in this art. According to the present invention the formed polymer ligand systems can be present as regards the units according to formulas I, II and IV in each of the three named forms. This means that in the case of a purely statistical copolycondensate containing units according to formulas I and II and optionally IV, there is a statistical distribution of the components according to the molar ratios of the initial products, taking into consideration the silicon groupings present in the case of units I and II according to formula III and the functionality of the cross-linking agent IV.

In the case of a so-called block copolycondensate, there is a formation of blocks of identical units according to formulas I and II and optionally IV.

Finally, a so-called mixed copolycondensate exhibits both structures of a statistical copolycondensate as well as of a block copolycondensate. The units according to formula I or formula II or formula IV can be present both as statistical and also block copolycondensate thereby.

Particular advantages as regards the availability of initial materials and the material properties are achieved with polymer ligand systems in which $R^1$ to $R^4$ stand for a group of the general formula

(V)

The preferred metal-containing groups which are bound in a complex manner to the polymer units according to formula II and formula I are one or several metal units VI of $FeX_3$, $FeX_2$, $CoX_3$, $CoX_2$, $NiX_2$, $RuX_3$, $RuX_2$, $RhX_3$, $RhX_2$, $RhX$, $Rh(diene)X$, $RhX(CO)$, $PdX_4$, $PdX_2$, $Pd^0$, $OsX_3$, $IrX_3$, $IrX$, $Ir(diene)X$, $IrX(CO)$, $PtX_4$, $PtX_2$, and $Pt^0$ in which X stands for Cl, Br, I, H, acetyl acetonate, acetate, 0.5 $SO_4$, $NO_3$, and CN, and diene stands for cyclooctadiene and norbornadiene (otherwise known as bicyclo (2,2,1) hepta-2,5-diene; $C_7H_8$, molecular weight=92.14, boiling point=88°-90° C.).

The complex structures formed by complex formation between metal units and polymer ligand systems are basically known from the complex chemistry of these metals and are familiar to the chemist skilled in the chemistry of complexes (Cf. e.g. the book series "Inorganic Syntheses", John Wiley & Sons, New York, Chichester, Brisbane, Toronto, Singapore, or "Inorganic Chemistry of the Transition Elements", Chemical Society, Burlington House, London W1V OBN). They can be described for the individual metals relevant to the invention e.g. by the following formulas: $FeX_3L_3$, $FeX_2L_4$, $CoX_3L_2$, $CoX_3L_3$, $CoX_2L_3$, $CoX_2L_4$, $NiX_2L_2$, $NiL_4$, $RuX_3L_3$, $RhX_3L_3$, $RhX_2L_3$, $RhXL_3$, $RhL_4{}^+X^-$, $PdX_4L_2$, $PdX_2L_2$, $PdL_4$, $OsX_3L_3$, $IrX_3L_3$, $IrXL_3$, $PtX_4L_2$, $PtX_2L_2$, and $PtL_4$, where X=Cl, Br, I, H, acetyl acetonate, acetate, $\frac{1}{2}$ $SO_4$, $NO_3$, and CN; and L =ligand.

The soluble complex structures known from the complex chemistry of these metals can naturally also be transferred onto the polymer-ligand-bound, insoluble metal units. This means in the case of the formed transition-metal complex catalysts of the invention that L represents a polymer ligand unit of formula I or formula II, which represent the anchor groups via which the previously named metal units are bound to the polymer matrix.

In the case of the heterogenized complex catalysts of the invention, it is advantageous for the catalytic properties if the above-named metal units according to formula VI are bound to the polymer matrix via at least one phosphine unit according to formula II in each instance.

A preferred embodiment of the invention provides that the metal units according to formula VI are bound in each instance to the polymer matrix only via phosphine units according to formula II.

It is advantageous for the practice of the invention the metal content in the polymer system is at least 0.01 % by weight and at the most 18 % by weight. Metal contents in the polymer system of at least 0.1 % by weight and at the most 10% by weight are especially preferred.

As regards the catalytic properties and the metal adhesion of the compounds of the invention, the phosphine units according to formula II are the decisive ligand components in the structure of the polymeric metal-matrix compound whereas the amine groupings assure advantageous physical properties, in particular, and also, in part, chemical properties of the polymer.

The composition of the compounds of the invention can be influenced via certain production measures, the distribution of the two ligand types according to formulas I and II resulting therefrom and via their stoichiometric ratio. It is basically known, of course, from complex chemistry that a phosphine ligand of the type of the ligand unit according to formula II (type: diphenylalkylphosphine) exhibits a considerably stronger complexing capacity than an amine ligand of the type of the ligand unit according to formula I. This fact must be taken into account in the conception of the polymeric metal complexes to be built up and in the selection of the production measures, because as a rule the phosphine ligand will always complex the central atom of the transition metal with precedence in the case of a competing situation.

The metal concentrations indicated take into account the fact that in addition to the ligands according to formulas II and I complexing the fixed metal centers according to formula VI, still other excess and non-complexing ligands according to formulas I and/or II are present in the polymer system. A special embodiment of the invention provides that no more ligand units according to formula II are present in the polymer system than are maximally required to build up the particular metal complex, so that the stoichiometric ratio between the ligands according to formula II and the metal is at least 1 : 1, but, as a function of the particular metal for Fe, Co, Rh, Pd, Pt, Ni, a maximum of 4 : 1. and for Ru, Os, Ir a maximum of 3 : 1 and that other ligands according to formula I are present in addition in the polymer system. In the case of a ratio of 1 : 1, amine units according to formula I must naturally also be used for building up the polymeric metal complex.

It can be advantageous in a number of polymeric catalysts, as a function of the type of the reaction to be catalyzed, e.g. as concerns the obtention of an improved metal adhesion or of improved selectivity properties, if excess polymer ligand units according to formula II above the ratio of 4:1 or 3:1 are also present in the polymer matrix. These excess ligands according to formula II can also be present in relation to the amine units according to formula I and the optionally present crosslinking agents both as statistical, block or mixed copolycondensates.

On the whole, the extreme values of the conceivable compositions are given on the one hand by the limit values of the molar ratio of tile units according to formula I to the units according to formula II of 95 : 5 mole % to 1.0 : 90 mole % and on the other hand by the possible metal contents of 0.01 to 18 % by weight.

The present invention is also concerned with methods of preparing the formed, polymeric transition-metal complex catalysts of the present invention described above. Initial metal compounds are used almost exclusively thereby which are relatively readily accessible from a preparative standpoint and are commercially available. The preparation of the monomer complex which precedes the polycondensation stage, that is, the formation of the polymer matrix, and which uses silicon-substituted monomer ligands of the formula

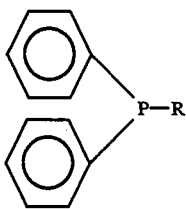

and optionally of the formula

takes place in the methods of the present invention according to known principles of transition-metal chemistry like those described in a general manner in the previously cited literature or in scientific publications on the complex chemistry of the metals named here.

A first method of preparing the formed polymeric metal complexes is characterized in that one or several hydrous or anhydrous metal compounds VII of $FeX_3$, $FeX_2$, $CoX_3$, $CoX_2$, $NiX_2$, $RuX_3$, $RuX_3$ $(Ch_3CN)_3$, $RuX_3$ $(C_6H_5CN)_3$, $M_3RhX_6$, $RhX_3$, $RhX_3$ $(Ch_3CN)_3$, $RhX_3(C_6H_5CN)_3$, $RhX_2$, $(RhX(diene))_2$, $M_2PdX_6$, $M_2PdX_4$, $PdX_2$, $OsX_3$, $OsX_3(C_3CN)_3$, $OsX_3(C_6H_5CN)_3$, $M_3IrX_6$, $IrX_3$, $IrX_3$ $(C_3CN)_3$, $IrX_3$ $(C_6H_5CN)_3$, $(IrX(diene))_2$, $M_2PtX_6$, $M_2PtX_4$, and $PtX_2$, in which X=Cl, Br, I, acetyl acetonate, acetate, ½ $SO_4$, $NO_3$, and CN; and diene =cyclooctadiene and norbornadiene; and M=H, Na, K, and $NH_4$;

are reacted to form the metal complex in a solvent or a solvent mixture having a preferably polar nature, optionally at elevated temperature, for a period or 1 min. to 48 hours, with a phosphine of the formula

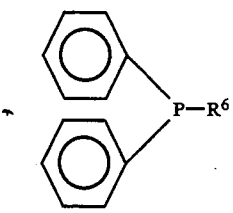

in which $R^6$ signifies a group of the formula

 (IX), $R^5$ has the same meaning as in formula III described above, $R^7$ signifies a linear or branched alkyl group with 1 to 5 C atoms, and the ratio between the number of moles of phosphine according to formula VIII and the number of moles of the totally complexly bound metal atoms in the metal compounds according to formula VII is at leat 1 : 1 to 1000 : 1, preferably 1 : 1 to 100 : 1;

to the solution thereby obtained there is then added an amino silane of the formula

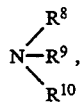

in which $R^8$ stands for H, $CH_3$, $C_2H_5$, $C_3H_7$ or a group of formula IX and $R^9$ and $R^{10}$ also stand for a group of formula IX in which $R^5$ and $R^7$ have the same range of meaning as in formula IX, and optionally one or several compounds of the formula

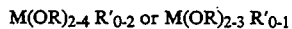 (XI), in which M is an Si, Ti, Zr or Al atom, R' is a linear or branched alkyl group with 1 to 5 C atoms or a phenyl group, R signifies a linear or branched alkyl group width 1 to 5 C atoms, and the ratio of the silicon atoms from the groups of formula IX to the metal atoms in the cross-linking agents IX is 1 : 0 to 1 : 20;

then an amount of water is added to the obtained solution under agitation which suffices at least for a complete hydrolysis and condensation, the resulting reaction mixture is then hydrolysed for a period of up to 6 hours, preferably at reflux temperature; then allowed to gel under further agitation at a temperature in the range of room temperature to 200° C. on the condition that it is compounded at the start of gelling or up to one hour thereafter with 10 to 2000, preferably 50 to 500 % by weight, relative to the entire amount of phosphine (VIII), aminoorganosilane (X) and, optionally, cross-linking agent (XI), with a solvent which is largely non-water-soluble but dissolves the reaction mixture which has gelled or started to gel in order to form a homogenizate;

then, immediately or in a time period of up to 10 hours, water in an amount of 100 to 2000, preferably 50 to 500 % by weight, relative to the total amount of phosphine (VIII), aminoorganosilane (X) and, optionally cross-linking agent (XI), is added to the viscous homogenizate, optionally with elevation of the originally adjusted temperature;

the organic phase containing the monomeric metal complex is then dispersed in the liquid two-phase system; the solid forming in the shape of spheres is separated from the liquid phase after a reaction time sufficient for this purpose at a temperature of room temperature to 200° C., then extracting, optionally width a low-boiling solvent, drying at room temperature to 250° C., optionally under protective gas or in a vacuum and tempering 1 to 100 hours at temperatures of 150° C. to 300° C. and/or classifying by size.

According to this first method, mixed or statistical copolycondensates are obtained as a function of the stoichiometry in relation to all polymer units according to formulas I and II present as well as, optionally, to groups according to formula IV present. It should be noted that a block formation takes place on the metal center on account of the complexing of the phosphine units according to formula II and, when hydrous metal compounds (VII) are used, a partial precondensation of the added monomeric phosphines according to formula VIII takes place even during their reaction with the metal component. However, when anhydrous metal compounds (VII) are used, the formation of a statistical distribution is to be assumed for phosphine units according to formula II which are optionally present above the highest coordination number and in relation to non-complexing or slightly complexing amine ligands (I) as well as any cross-linking groups (IV) which are optionally present.

Instead of the alkoxy silyl compounds, the corresponding halogenide or phenoxy compounds can also be used in principle as initial materials for the method; however, their use offers no advantages but rather can cause problems, e.g. in the case of the chlorides, on account of the hydrochloric acid liberated during hydrolysis.

The hydrolysis of the initial materials and optional cross-linking agent or agents must be carried out in a solvent which is miscible with water to a great extent but which dissolves the initial materials. Alcohols are preferably used thereby which correspond to the alkoxy groupings on the monomeric precursors of the initial materials or on the metal atoms of the optionally used cross-linking agents.

Methanol, ethanol, n- and i-propanol, n- and i-butanol or n-pentanol are especially suitable. Mixtures of such alcohols can also be used. Instead of alcohols, other polar solvents which are miscible with water to a great extent can also be used; however, this is not very logical for engineering reasons because the solvent mixtures which are produced with the alcohol hydrolytically split off.

The hydrolysis is preferably carried out with an excess of water above the stoichiometrically required amount. The amount of water necessary for hydrolysis depends on the hydrolysis speed of the phosphine (VIII), amine (X) and cross-linking agent (XI) used in such a fashion that as tile amount of water increases, a more rapid hydrolysis occurs; however, an upper limit can be given due to separation and formation of a two-phase system. Due to the two aspects cited, somewhat less water by weight is used in practice than organosilanes plus cross-linking agent. The duration of the hydrolysis is a function of the tendency of the initial substances and/or cross linking agents to hydrolyze and of the temperature. The readiness for hydrolysis and therewith the hydrolysis speed is especially a function of the type of the alkoxy groups in silicon or titanium, zirconium and aluminum position; the methoxy group hydrolyses the most rapidly thereby. In addition, the duration of the total process of hydrolysis and polycondensation is also a function of the basicity of the aminoorganosilane. As is known, amines function as condensation accelerators so that they can bring about a self-catalysis.

Hydrolysis and polycondensation are generally accelerated by the addition of bases, preferably of ammonia, or of inorganic or organic acids, but also by the catalytically active metal itself, or by the addition of customary condensation catalysts such as e.g. dibutyl tin diacetate.

The requirement of maintaining the initial substance, which is dissolved in solution and compounded with water, at a certain temperature under continuing agitation therefore has the result that the speed of the polycondensation, indicated by gelling, is temperature-dependent.

The temperature to be used in the hydrolysis phase or gelling phase is empirically determined and set in the individual instance. It should be selected in such a manner that a gel-like mass is retained in the following method step, the so-called forming phase.

The forming phase, which proceeds with the conversion of the coherent, metal-containing, gel-like mass permeated by liquid into separate, spherical particles begins with the compounding of the reaction mixture which has gelled or started to gel with a solvent, in the provided amount, which is largely non-water-soluble but dissolves the reaction mixture to a sufficient extent.

Suitable solvents are e.g. linear or branched alcohols with 4 to 18 C atoms or phenols, linear or branched symmetric or asymmetric dialkyl ethers as well as di- or triethers (such as ethylene glycol dimethyl ether), chlorinated or fluorinated hydrocarbons, aromatics or mixtures of aromatics substituted with one or several alkyl groups such as e.g. toluene or xylene, symmetric or asymmetric ketones which are largely non-miscible with water.

However, a linear or branched alcohol with 4 to 12 C atoms, toluene, ethyl benzene or o-, m-, p-xylene or mixtures thereof are added with preference to the reaction mixture which has gelled or started to gel.

This addition of solvent brings about, after the homogenization with the reaction mixture, a dilution and therewith a distinct slowing of the condensation reaction proceeding with the increase in viscosity.

The measuring of the amount of this solvent used in the forming phase depends in particular on which particle size is desired for the formed, polymeric transitional-metal complex catalyst. It can be considered a rule of thumb that little solvent is to be used for coarse particles (i.e., spheres with a fairly large diameter) and a lot of solvent is to be used for fine particles (i.e., spheres with a rather small diameter). In addition, the intensity with which the viscous homogenizate of the forming reaction product and the largely non-water-soluble solvent is dispersed in the aqueous phase also influences the particle size. The formation of a rather fine particle is favored by vigorous agitation. In order to stabilize the aqueous dispersion of the organic phase containing siloxane, one of the known dispersing agents such as long-chain carboxylic acids or their salts or polyalkylene glycols can be added in customary concentrations.

The preferred temperature at which the dispersing of the organic phase containing siloxane is carried out in the aqueous phase and at which spherical solid is formed from the disperse phase is as a rule the reflux temperature of the entire mixture. Basically, however, the same temperatures as in the gelling stage can be used. The total time of dispersing stage and postreaction is as a rule 0.5 to 10 hours.

Both the gelling and the forming can be carried out at normal pressure or a superpressure which corresponds to the sum of the partial pressures of the components of the reaction mixture at the particular temperature used.

The separation of the spherically formed, moist product from the liquid dispersing agent can take place by means of customary measures such as decanting, filtering off or centrifuging. In addition, however, the liquid phase can also be removed from the reactor and the remaining solid in it treated once or several times with a low-boiling extraction agent, preferably a low-boiling alcohol, in order to facilitate the later drying of the formed catalyst by means of an at least partial exchange of the usually relatively high-boiling solvent of the forming phase by the low-boiling extraction agent.

The drying can basically be carried out at room temperature to 250° C., optionally under protective gas or in a vacuum. For hardening and stabilizing, the dried, formed solid can be tempered at temperatures of 150 to 300° C.

The dried and/or tempered product can be classified in customary devices into various particle size fractions. One or the other of the workup measures of extraction, drying, tempering and classification can be eliminated, depending on the circumstances. A classification can be carried out on liquid-moist, dry or tempered product.

According to a variant of the method of the invention, a part or also the entire amount of the solvent which is largely non-water-soluble and is to be added at or after the start of gelling is added to the reaction mixture already in the hydrolysis stage in addition to the solvent used in it. In the case of a partial addition, the remainder is added after the start of gelling. In the extreme case of the addition of the entire amount, the dispersing agent water can be added at or after the start of gelling. This variant s used with preference when the mixture of the Si-substituted monomer complex prepared and of the optionally present, excess phosphine according to formula VIII and amine (X) as weal as optional cross-linking agents (XI) exhibits an extraordinarily high tendency toward hydrolysis and polycondensation.

As concerns the adjustment and fixing of a certain defined ligand sphere around the polymer-bound metal center, it can be especially advantageous if, in accordance with a variant of the method described above, the monomeric phosphine complex obtained after reaction with the phosphine according to formula VIII with the metal compound according to formula VII and the excess phosphine amount according to formula VIII, which is optionally still present in the mixture and is not required for complex formation, are at first precondensed up to the maximum ratio of phosphine (VIII) to metal compound (VII) of 1000 : 1, optionally after the addition of one or several of the compounds of general formula XI. To this end, a hydrous metal compound or anhydrous metal compounds of formula VII in a preferably polar solvent or solvent mixture is/are reacted with a phosphine of general formula VIII at a molar ratio between the number of moles of phosphine units (VIII) and the number of moles of the totally complex-bound metal of 1 : 1 to 1000 : 1, preferably 1 : 1 to 100 : 1 for a period of 1 min. to 48 hours; then a part or the complete amount of one or several of the compounds of general formula XI is optionally added to the solution of the formed, monomeric metal complex, this mixture is precondensed in the presence of an amount of water insufficient for complete hydrolysis, preferably from 1 to 100 mole % of the amount required for this, for a period of 5 min. to 48 hours at room temperature to 200° C.; then an amino silane of formula X, optionally the remaining or complete amount of one or more of the compounds according to formula XI, optionally more solvent and in any case more water are added, the mixture hydrolyzed again for a period of up to 4 hours, preferably at the reflux temperature of the reaction mixture, and then the rest of the procedure described above for the first method is followed as regards gelling and further treatment of the condensate which forms thereby.

The precondensation can generally be accelerated by the addition of a slight amount of an acidic or basic or metal-containing condensation catalyst.

Suitable catalysts are inorganic or organic acids or bases or also tin compounds. The amount of water used for precondensation depends on which degree of oligomerization, that is, which block size is to be achieved. When more water is used for the precondensation, larger units naturally are produced than when less water is used. An amount of water introduced by an initial metal component according to formula VII containing water of crystallization must, of course, also be considered in this connection when selecting tile amount of water used for precondensation. According to a variant of the method of the invention, the addition of free water is eliminated in the precondensation and it is carried out only with the water introduced by the metal component (VII) containing water of crystallization.

According to a further method variant, the amount of water used for precondensation, exceeding the optionally present amount of water of crystallization, is added right at the start of the reaction of the metal component (VII) with the phosphine (VIII) so that the formation of the monomer complex and its precondensation, the precondensation of the excess ligands as well as that of the optionally added compound(s) according to formula XI take place simultaneously. The complete hydrolysis and condensation are carried out directly thereafter.

The duration of precondensation generally depends, as already described above, on the readiness for hydrolysis of the monomeric components and the temperature.

A second method of the invention provides that one or several hydrous or anhydrous metal compounds of formula VII are reacted for a period of 1 min. to 48 hours in a preferably polar solvent with a phosphine of general formula VIII in a ratio between the number of moles of phosphine units (VIII) and the number of moles of the totally complex-bound metal atoms of 1 : 1 to x : 1, where x represents the particular metal-specific maximum coordination number in the particular metal complex; a part or the complete amount of one or several of the compounds of formula XI is optionally added to the solution of the monomeric metal complex formed and this mixture is precondensed in the presence of an amount of water insufficient for complete hydrolysis, preferably from 1 to 100 mole % of the amount required for this for a period of 5 min. up to 48 hours at room temperature to 200° C.; then the amount of phosphine of formula VIII exceeding the maximum coordination number of the metal, optionally the remaining or complete amount of one or several of the compounds according to formula XI as well as an amino silane of formula X, optionally more solvent and in any case more water are added; the mixture is hydrolyzed again for a period of up to 4 hours, preferably at the reflux temperature of the reaction mixture, and then the rest of the procedure described above for the first method is followed as regards gelling and further treatment of the condensate which forms thereby.

Of course, in this and in all subsequent precondensation variants an acidic, basic or metal-containing condensation catalyst can also be added or the precondensation can be carried out only with the water of crystallization of a hydrous initial metal compound or the precondensation can be carried out parallel in time with the reaction of the metal component (VII) with the phosphine (VIII).

A third method of the invention, according to which so-called block copolycondensates are obtained where in the block copolycondensates there is a formation of blocks of the same units according to formulas I and II and optionally of one or several units according to formula IV, provides that the monomeric metal complex obtained from the reaction of the metal compound of formula VII with the phosphine component of formula VIII (according to the first method described above) is precondensed together with any optionally present, excess phosphine (VIII) during or after its preparation, and an amino silane of formula X as well as optionally one or several compounds of formula XI are precondensed for a period of 5 min. to 48 hours at room temperature to 200° C. independently of each other without or using a solvent in the presence of an amount of water insufficient for complete hydrolysis, preferably in the presence of 1 to 100 mole % of the amount required for this, then the individual precondensed components are combined and then, after the addition of so much water that at least the amount of water stoichiometrically necessary for a complete hydrolysis is present and, optionally, after more solvent, the complete hydrolysis and polycondensation as well as further workup (according to the first method described above) are carried out.

A fourth method of the invention, which is intended to compensate on one hand in particular a distinctly different gelling behavior of the formed metal complex containing phosphine groups and of optionally present, excess phosphine (VIII), and on the other hand an amino silane (X) as well as of one or several compounds (XI), provides that the metal compound (VII) is reacted with the phosphine according to the first method described above, then is precondensed at the same time or subsequently in the presence of an amount of water insufficient for complete hydrolysis, preferably in the presence of 1 to 100 mole % of the amount required for this, for a period of 5 min. to 48 hours at room temperature to 200° C., and, independently thereof, the amino silane (X) is precondensed, optionally as a mixture with one or several compounds of formula XI without or using a solvent, in the presence of an amount of water insufficient for complete hydrolysis, preferably in the presence of 1 to 100 mole % of the amount required for this for a period of 5 min. to 48 hours at room temperature to 200° C., then the two precondensates are combined and then, after the addition of more water and, optionally, more solvent, so that at least the amount of water stoichiometrically necessary for a complete hydrolysis is present, the complete hydrolysis and polycondensation as well as a further workup according to the first method are carried out.

A further method variant of the invention provides that an anhydrous metal component (VII) is reacted with the phosphine component (VIII) in a manner already described but is not precondensed, and at the same time, but independently of each other, an amino silane (X) and, optionally, one or several compounds (XI) are precondensed without or using a solvent in the presence of an amount of water insufficient for complete hydrolysis, preferably in the presence of 1 to 100 mole % of the amount required for this, for a period of 5 min. up to 48 hours at room temperature to 200° C., the non-precondensed, metal-containing mixture and the two precondensates are combined with each other and then, after the addition of more water and, optionally, more solvent, so that at least the amount of water stoichiometrically necessary for a complete hydrolysis and polycondensation is present, the complete hydrolysis and polycondensation as well as a further workup according to the first method are carried out.

The different types of precondensation co-determines the structures of the polymers subsequently obtained in a decisive manner. The latter, for their part, influence the catalytic properties of the catalysts obtained in this manner and, in addition and among other things, also the adhesion of the metal or metals on the polymer ligand carrier.

This also applies to a fifth method of the invention according to which a hydrous or anhydrous metal compound (VII) in a preferably polar solvent is reacted with a phosphine (VIII) in the presence of an amino silane (X) as well as, optionally, one or several of the compounds (XI) for a period of 1 min. to 48 hours according to the first method described above, an amount of water sufficient at least for the complete hydrolysis and condensation is added to the solution under agitation and then the procedure of the first method described is followed.

Of course, a purposeful precondensation can also be carried out in this method variant, e.g. in order to compensate a different gelling behavior of the components, in such a manner that a precondensation is carried out during the reaction of the components to the monomeric metal complex (according to the first method) or immediately thereafter by means of the addition of an amount of water insufficient for complete hydrolysis, preferably of 1 to 100 mole of the amount required for this, for a period of 5 min. up to 48 hours at room temperature to 200° C. (that is, according to the variant of the first method), and then, after the addition of more water and, optionally, more solvent, so that at least the amount of water stoichiometrically necessary for a complete hydrolysis and polycondensation is present, the complete hydrolysis and polycondensation according to the first method are carried out.

A special method variant results in the preparation of polymeric, formed, heterogenized complex catalysts in which according to formula VI X = H or the metal is present complex-bound in zero-valent form; the method provides a treatment of the monomeric metal complex primarily prepared according to the first method described above before or after an optionally performed precondensation with a reducing agent, optionally at elevated temperature and/or superpressure for a period of 1 min. to 48 hours and follows this (as in the first method) with the further hydrolysis, polycondensation and workup.

Suitable reducing agents are e.g. formaldehyde, hydrazine, alkali- or alkaline-earth metal boron hydride, borane compounds, formates, aluminum hydrides and also only alcohols or hydrogen. Moreover, in addition to the reducing agent, a separate acid acceptor can also be added to the solution containing metal complex in addition to the already present amine (X) or excess phosphine (VIII). The following are suitable, for example: alkali- or alkaline-earth metal hydroxides, alkali-metal- or alkaline-earth metal hydrides, complex boron or aluminum hydrides, alkali- or alkaline-earth metal carbonates or -bicarbonates, primary, secondary or tertiary amines.

According to a modification of the method variant indicated above, the monomeric metal complex primarily prepared according to the methods described above is at first hydrolyzed and polycondensed under forming conditions and suspended, before or after at least one of the development stages provided in the first method, in water or a solvent, preferably a lower alcohol or a mixture thereof with water and subjected to the reducing treatment described above, optionally under superpressure. Thus, the reductive treatment is carried out after the formation of the formed complex catalyst (that is, after the addition of the dispersing water following the procedure of the first method described above) or also after the extraction of the produced and formed metal complex or also after its drying and optional tempering, namely in suspension with a suitable solvent as suspending agent. Water or a lower alcohol or a mixture of such an alcohol with water is used for this with preference.

An especially important embodiment of all methods of the invention provides that the spherical complex, which is still moist or wet with solvent and water, is subjected to a temperature treatment.

This treatment under "steaming" or digesting conditions also serves primarily for an improvement of the mechanical strength and of the porosity of the formed material and can also be carried out in the last dispersion of the preparation process present, which dispersion contains a liquid phase and the solid product phase, or in water alone. The temperature treatment can also be combined with a reductive treatment.

The embodiment of a posttreatment of the formed complex catalysts obtained but not dried which is described above thus consists in subjecting the complex formed in the form of spheres in the presence of at least the component water or the liquid phase which was present last in the preparation process as vapor or liquid to a temperature treatment for 1 hour to 1 week at temperatures of 50°-300° C., preferably 100°-200° C., optionally under superpressure. The presence of an acidic, basic or additional metal-containing catalyst can be advantageous thereby. This posttreatment can be carried out in conjunction with a reductive treatment. A preferred method is the hydrogen treatment; in addition, mixtures between hydrogen and inert gases can also be used. An especially effective reduction can take place by using sodium boron hydride; a combination of this agent with $H_2$ is also possible.

The novel, formed polymeric transition-metal complex catalysts are characterized in particular using quantitative hydrolysis yields, elementary analyses, and the catalytic behavior, which is complex-specific comparable in each instance to that of an analogous, homogeneous complex catalyst.

Optically, there is no difference between the polymeric catalysts obtained according to the various preparation methods described above. An important characteristic of the catalysts prepared according to the methods of the present invention is the fact that the complex-bound metal is distributed in a homogeneously dispersed manner, that is, uniformly over the formed particle. In order to make possible the access of the educts to be reacted to the inner catalytic centers, it is necessary that the formed catalysts exhibit suitable physical properties. In addition to a suitable particle diameter of 0.01 to 3.0 mm, preferably 0.05 to 2.0 mm, this includes a BET specific surface of >0 to 1000 $m^2/g$, preferably >0 to 700 $m^2/g$, a specific pore volume of 0.01 to 6.5 ml./g as well as a bulk density of 50-1000 g/l, preferably 100 to 800 g/l. The pore diameter is from >0 to 1000 nm. The thermal stability of the formed catalysts is more than 130° C. in air and more than 200° C. under an atmosphere of inert gas, as a function of the formed complex type.

The formed transition-metal complex catalysts of the invention constitute valuable catalysts for chemical reactions such as reactions of hydroformylation, hydrogenation, oligomerization, carbonylation, hydrosilylation, carboxymethylation and isomerization as well as for reactions of CO or $CO_2$ with $H_2$. Therefore, a corresponding use constitutes further subject matter of the invention.

Metal-specifically, a different suitability of the systems of the inventions for the above-named reactions is apparent thereby in exact analogy to homogeneous catalysts. The formed, polymeric metal complex catalysts can be used in suspension or in a fixed bed or in a fluid bed for reactions in liquid or gaseous phase.

The invention is explained in more detail in the following using examples of embodiments.

EXAMPLES

Example 1

Statistical copolycondensate 14.54 g (0.03 mole) $(RhCl(C_8H_{12}))_2$ ($C_8H_{12}$=cyclooctadiene) and 62.7 g (0.18 mole) $(C_6H_5)_2P(CH_2)_3Si(OCH_3)_3$ were combined in 100 ml ethanol. The mixture was heated in a 4 liter glass container with agitator and reflux condenser to reflux temperature and agitated 1 hour at this temperature. Then 223.1 g (0.35 mole) $N((CH_2)_3Si(OC_2H_3)_3)_3$, 250 ml ethanol, and 73.8 g (0.35 mole) $Si(OC_2H_5)_4$ were added to the mixture. The clear solution was reheated to reflux temperature and then compounded with 100 ml desalinated water.

It was agitated 10 minutes more under reflux, then cooled down to 75° C. and agitated further until the start of gelling. 2 min. after the start of gelling, 750 ml octanol-1 were added to the mixture and after a further 5 min, 700 ml desalinated water were added. The 2-phase mixture was heated under agitation (500 rpms) back to reflux temperature, agitated 2 hours at this temperature, then cooled down and transferred into a 4 liter pressure container. The suspension was slowly agitated 24 hours at 130° C. and an inherent pressure of approximately 8 bars, then cooled down again and the liquid phase removed by suction from tile solid present in the form of spheres. After two extractions with 2 liters ethanol each time, the product was transferred into a drying oven and dried for 8 hours at first at 80° C. and then for 16 hours at 130° C. under an atmosphere of $N_2$. 92.6 g (approximately 99.1% of theoretical) of a formed, polymeric rhodium complex catalyst were obtained consisting of polymer units of the formula $$RhCl((C_6H_5)_2P-(CH_2)_3SiO_{3/2}\cdot 2N((CH_2)_3SiO_{3/2})_3\cdot SiO_2)_3,$$

of which 98% exhibited a grain size of 0.3 to 1.8 mm.
Specific surface: 612 $m^2/g$
Specific total pore volume: 2.2 ml/g
Bulk density: 395 g/l

| Elementary analyses: | % Rh | % Cl | % P | % Si |
|---|---|---|---|---|
| Theory: | 3.3 | 1.1 | 3.0 | 24.3 |
| Observed: | 3.4 | 1.1 | 2.9 | 23.8 |

Example 2

Mixed copolycondensate 1.66 g (0.005 mole) $RhCl_3 (CH_3CN)_3$ and 9.1 g (0.1 mole) $(C_6H_5)P-(CH_2)_3Si(OC_2H_5)_3$ were combined in 100 ml ethanol. The mixture was heated to reflux temperature and compounded with 5 ml desalinated water. The solution was agitated one hour at this temperature, then compounded with 63.0 g (0.1 mole)

N((CH$_2$)$_3$Si(OC$_2$H$_5$)$_3$)$_3$ as well as with a further 20 ml water and agitated 25 min. further under reflux. It was cooled down to 70° C. and agitated at this temperature at 50 rpms until the start of gelling. Immediately after the start of gelling, 160 ml xylene (industrial mixture) were added to the forming gel and after one more minute 300 ml water were added. The 2-phase system was agitated 1 hour under reflux, then cooled down and transferred into a 3 liter pressure container. The suspension was maintained at 140° C. for 48 hours and then dried analogously to example 1 and tempered a further 12 hours at 160° C. 56.8 g (96.9 % of theoretical) of a formed, polymeric rhodium complex catalyst were obtained consisting of polymer units of the formula

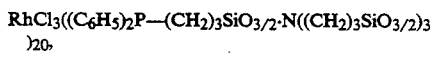

RhCl$_3$((C$_6$H$_5$)$_2$P—(CH$_2$)$_3$SiO$_{3/2}$·N((CH$_2$)$_3$SiO$_{3/2}$)$_3$)$_{20}$, of which 98% exhibited a grain size of 0.3 to 1.8 mm.
Specific surface: 690 m$^2$/g
Specific total pore volume: 1.5 ml/g
Bulk density: 400 g/l

| Elementary analyses: | % Rh | % Cl | % P |
|---|---|---|---|
| Theory: | 0.9 | 0.9 | 5.3 |
| Observed: | 0.9 | 0.8 | 5.1 |

Example 3
Block copolycondensate 0.88 g (0.002 mole) (Rh(O$_2$CCH$_3$)$_2$)$_2$, 40.5 g (0.1 mole) (C$_6$H$_5$)$_2$P—CH$_2$Si(OC$_3$H$_7$)$_3$ and 7.4 g (0.05 mole) (CH$_3$)$_2$Si(OC$_2$H$_5$)$_2$ were combined in 70 ml isopropanol. The solution was compounded with 8 ml desalinated water, heated to reflux temperature and agitated 3 hours under reflux. Parallel thereto, 24.1 g (0.05 mole) HN((CH$_2$), Si(OCH$_3$)$_3$)$_2$ and 5 ml 1% aqueous NH$_3$ solution were combined in 50 ml isopropanol and also agitated 2 hours under reflux. Then, the two precondensates were combined, 15 ml water added and the mixture agitated further under reflux until the start of gelling. 10 min. after the start of gelling, 200 ml sec.-butanol were added and after a further 30 min., 150 ml desalinated water were added. The 2-phase system was agitated a total of 10 hours under reflux, then cooled down and the solid separated from the liquid phase, and then dried analogously to example 2, 46.2 g (98.5 % of theoretical) of a polymeric complex catalyst were obtained consisting of polymer units of the formula

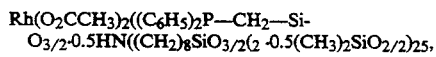

Rh(O$_2$CCH$_3$)$_2$((C$_6$H$_5$)$_2$P—CH$_2$—SiO$_{3/2}$·0.5HN((CH$_2$)$_8$SiO$_{3/2}$(2 -0.5(CH$_3$)$_2$SiO$_{2/2}$)$_{25}$, with a grain size distribution of 0.1 mm to 1.8 mm.
Specific surface: 131 m$^2$/g
Specific total pore volume: 0.5 ml/g
Bulk density: 490 g/l

| Elementary analyses: | % Rh | % P | % Si |
|---|---|---|---|
| Theory: | 0.9 | 6.6 | 15.0 |
| Observed: | 0.9 | 6.3 | 14.7 |

Example 4

15.7 g (0.09 mole) PdCl$_2$, 62.7 g (0.18 mole) (C$_6$H$_5$)$_2$P—(CH$_2$)$_3$Si(OCH$_3$)$_3$ and 73.7 g (0.35 mole) Si(OC$_2$H$_5$)$_4$ were combined in 300 ml methanol. The mixture was heated to reflux temperature and agitated at first under reflux until all PdCl$_2$ had dissolved. Then 10 ml water were added to the solution and the mixture precondensed under agitation at reflux temperature for 2 hours at first. Then 178.3 g (0.35 mole) N((CH$_2$)$_3$Si(OCH$_3$)$_3$)$_3$ as well as a further 100 ml water were added and the mixture agitated 25 min. further under reflux. Then the solution was cooled down to 60° C., agitated further at this temperature until the start of gelling. Immediately after the start of gelling, 500 ml 2-ethylhexanol were added to the forming gel, and after a further 3 minutes 500 ml water were added. The 2-phase system was reheated to reflux temperature and agitated 2 hours at this temperature. After proceeding further analogously to the method of example 1, with the difference of a 48 hour posttreatment at 140° C., 192.9 g (99.1 % of theoretical) of a formed, polymeric palladium complex catalyst were obtained consisting of polymer units of the formula

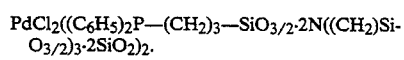

PdCl$_2$((C$_6$H$_5$)$_2$P—(CH$_2$)$_3$—SiO$_{3/2}$·2N((CH$_2$)Si-O$_{3/2}$)$_3$·2SiO$_2$)$_2$.

95% of the formed spheres exhibited a diameter of 0.05 to 1.0 mm.
Specific surface: 738 m$^2$/g
Specific total pore volume: 4.6 ml/g
Mesopore volume: 2.4 ml
Macropore volume: 2.2 ml
Bulk density: 230 g/l

| Elementary analyses: | % Pd | % P | % N |
|---|---|---|---|
| Theory: | 4.9 | 2.9 | 2.6 |
| Observed: | 4.8 | 2.9 | 2.4 |

Example 5

2.94 g (0.01 mole) Na$_2$PdCl$_4$, 15.6 g (0.04 mole) (C$_6$H$_5$)$_2$P—(CH$_2$)$_3$—Si(OC$_2$H$_5$)$_3$, 17.03 g (0.04 mole) HN((CH$_2$)$_3$Si(OC$_2$H$_5$)$_3$)$_2$ and 16.51 g (0.08 mole) C$_3$H$_7$Si(OC$_2$H$_5$)$_3$ were combined in 60 ml ethanol. The mixture was heated in a 0.5 liter glass container to reflux temperature and agitated 20 min. at this temperature. 30 ml hexanol-1 and 15 ml water were added, the solution then cooled down to 40° C. and agitated further until the start of gelling. Immediately after the start of gelling, a further 80 ml hexanol were added, and after half a minute of homogenizing 120 ml water were added. The 2-phase system was heated to reflux temperature and agitated 3 hours at this temperature. The mixture was then cooled down and the formed polymer complex filtered off from the liquid phase and washed twice with 300 ml ethanol per time. After an 8 hour drying at 100° C. and a 16 hour drying at 140° C. under an atmosphere of N$_2$, 28.6 g (97.7 % of theoretical) of a polymeric complex were obtained consisting of units of the formula

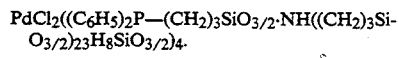

PdCl$_2$((C$_6$H$_5$)$_2$P—(CH$_2$)$_3$SiO$_{3/2}$·NH((CH$_2$)$_3$SiO$_{3/2}$)$_2$·3H$_8$SiO$_{3/2}$)$_4$.

98% of the spheres formed exhibited a diameter of 0.2 to 1.6 mm.
Specific surface: 326 m$^2$/g
Bulk density: 405 g/l

| Elementary analyses: | % Pd | % P | % N |
|---|---|---|---|
| Theory: | 3.7 | 4.3 | 2.0 |
| Observed: | 3.8 | 4.2 | 2.1 |

Example 6

Precondensation without the addition of water only with water of crystallization 22.26 g (63.2 mmoles) $IrCl_3H_2O$ were dissolved in a 3 liter glass container with double-jacket heating, KPG agitator and reflux cooler in 500 ml ethanol under an argon atmosphere at 60° C. The clear solution was first compounded with 66.0 g (189.5 mmoles) $(C_6H_5)_2P—(CH_2)_3Si(OCH_3)_3$, and after 5 min. with 39.5 g (189.5 mmoles) $Si(OC_2H_5)_4$ and subsequently agitated for a period of 1 hour at reflux temperature at which time reaction and precondensation took place simultaneously. Then 39.5 g $(Si(OC_2H_5)_4)$, 238.8 g (379.0 mmoles) $N((CH_2)_3Si(OC_2H_5)_3)_3$ and 130 ml $H_2O$ were added once more. After 10 minutes of further agitation under reflux temperature, the solution was cooled down to 70° C. and agitated further at this temperature at 100 rpms until the start of gelling.

Immediately after the start of gelling, 700 ml octanol-1 (60° C. warm) were added to the forming gel and the agitation speed raised to 750 rpms. After a further minute of homogenizing, 1200 ml water (in which 1.2 g polyvinyl alcohol (MOVIOL ®)) had been dissolved) were added to the viscous solution. The 2-phase system was heated to reflux temperature and agitated a further 2 hours at this temperature. After it had cooled off, the solid present in the form of small yellow spheres and the mother solution were separated by decanting, and solvent-moist solid and mother solution divided into 2 equal parts. One half of the named solid as well as one half the amount of mother solution were transferred into a 5 liter autoclave (for further processing of the other product half see example 7) and agitated with stirring at a temperature of 135° C. for a period of 48 hours under inherent pressure. The mixture was cooled off, the liquid phase removed from the solid by suction, and the latter washed twice with 1 liter ethanol each time. The mixture was then dried 12 hours at 100° C. and 12 hours at 130° C. under an atmosphere of $N_2$. 103.0 g (99.5 % of theoretical) product were obtained of which over 98% was present in the form of yellow spheres with a sphere diameter of 50 μm to 0.6 mm.

| Elementary analyses: | % Ir | % P | % H | % C | % Cl | % Si |
|---|---|---|---|---|---|---|
| Theory: | 5.9 | 2.8 | 4.8 | 36.3 | 3.2 | 23.1 |
| Observed: | 5.8 | 2.8 | 4.7 | 35.8 | 3.3 | 22.8 |

Bulk density: 250 g/l
Specific starface: 648 m²/g
Pore volume (pore diameter greater than 2 nm): 3.4 ml/g
Formula for polymer unit:

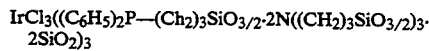

$IrCl_3((C_6H_5)_2P—(Ch_2)_3SiO_{3/2}\cdot 2N((CH_2)_3SiO_{3/2})_3\cdot 2SiO_2)_3$

Example 7

The second half of the polymeric product prepared in example 6 was subjected to a reductive treatment with sodium boron hydride. To this end, the formed, solvent-moist solid was transferred together with the second half of the mother solution into an autoclave and 35 g $NaBH_4$ were added. The immediately formed hydrogen was first let off and rinsed twice with argon. The mixture was then heated to 140° C., during which a pressure of 28 bars developed and was agitated 24 hours at this temperature. After cooling off of the mixture and removal of the liquid phase by suction, the mixture was washed twice with 1 liter ethanol each time, twice with 1 liter water each time and twice again with 1 liter ethanol each time, and then the bright yellow solid was dried 12 hours at 100° C. as well as 12 hours at 130° C. under an atmosphere of $N_2$. 99.8 g (99.5 % of theoretical) polymer complex were obtained consisting of polymer units of the formula

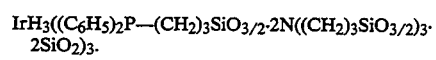

$IrH_3((C_6H_5)_2P—(CH_2)_3SiO_{3/2}\cdot 2N((CH_2)_3SiO_{3/2})_3\cdot 2SiO_2)_3$.

98% of the product obtained was present in the form of spheres with a diameter of 50 μm to 0.6 mm.

Bulk density: 210 g/l

| Elementary analyses: | % Ir | % P | % Cl |
|---|---|---|---|
| Theory: | 6.1 | 2.9 | 0.0 |
| Observed: | 6.0 | 2.8 | 0.02 |

Specific surface: 483 m²/g

Example 8

17.49 g (63.2 mmoles) $RuCl_3\ 3H_2O$ were dissolved in 125 ml ethanol at 60° C., then combined with 66.1 g (189.6 mmoles) $(C_6H_5)_2P—(CH_2)_3Si(OCH_3)_3$ and with 5 ml water. The solution was then precondensed for a period of 2 hours at reflux temperature under agitation. Parallel thereto, 164.8 g (379.0 mmoles) $Si(OC_2H_5)_4$, dissolved in 50 ml ethanol, were precondensed by reaction with 5 ml water and 238.8 g (379.0 mmoles) $N((CH_2)_3Si(OC_2H_3)_3)_3$, dissolved in 200 ml ethanol, were precondensed by reaction with 8 ml water for a period of 2 hours at reflux temperature under agitation in each instance. Thereafter, all 3 precondensates were combined in a 3 liter glass container with double-jacket heating, KPG agitator and reflux cooler, the mixture compounded with a further 50 ml water and agitated again for 10 min. under reflux. Thereafter, the mixture was cooled down to 70° C. and agitated further until the start of gelling. 5 min. after the start of gelling, 750 ml octanol were added to the forming gel, and after a further 2 min. 1300 ml water were added. The 2-phase system was reheated to reflux temperature and agitated 1 hour at this temperature. Then the batch was cooled down and the formed solid as well as the mother solution were divided into 2 equal parts each. One part each thereof was transferred into a 5 liter autoclave and agitated 24 hours in it at 150° C. After cooling off the mixture, removal of the liquid phase, triple extraction of the yellow solid with 500 ml ethanol each time, and an 8 hour drying at 110° C. as well as a 1 hour drying at 140° C., 100.3 g (99.7 % of theoretical) polymer complex were obtained consisting of polymer units of the formula

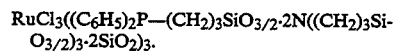

$RuCl_3((C_6H_5)_2P—(CH_2)_3SiO_{3/2}\cdot 2N((CH_2)_3SiO_{3/2})_3\cdot 2SiO_2)_3$.

96% of the product obtained was present in the form of spheres with a diameter of 0.2 to 1.2 mm.

Bulk density: 320 g/l

Total pore volume: 3.4 ml/g(pore diameter: 2 to 1000 nm)

| Elementary analyses: | % Ru | % P | % H | % C | % Cl | % Si | % N |
|---|---|---|---|---|---|---|---|
| Theory: | 3.2 | 2.9 | 4.9 | 37.3 | 3.3 | 23.8 | 2.6 |
| Observed: | 3.2 | 2.8 | 4.8 | 36.8 | 3.3 | 23.7 | 2.5 |

Example 9

The other half of the spherical, still solvent-moist raw product prepared in example 8 was transferred together with the other half amount of mother solution into an autoclave and then compounded with 20 g sodium boron hydride. After a process analogous to example 7, 97.0 g (99.6% of theoretical) polymer complex were obtained consisting of units of the formula $RuH_2((C_6H_5)_2P-(CH_2)_3SiO_{3/2}\cdot 2N((CH_2)_3Si-O_{3/2})_3\cdot 2SiO_2)_3$.

Bulk density: 185 g/l

| Elementary analyses: | % Ru | % P | % H | % C | % Si | % Cl | % N |
|---|---|---|---|---|---|---|---|
| Theory: | 3.3 | 3.0 | 5.1 | 38.6 | 24.6 | 0 | 2.7 |
| Observed: | 3.2 | 2.9 | 5.0 | 38.2 | 23.3 | 0.02 | 2.8 |

Example 10

36.1 g (95 mmoles) $(NH_4)_2PtCl_4$, 132.4 g (380 mmoles) $(C_6H_5)_2P-(CH_2)_3Si(OCH_3)_3$ and 158 3 g (760 mmoles) $Si(OC_2H_5)_4$ were combined in a 3 liter autoclave in 400 ml ethanol. The mixture was first agitated 1 hour at 100° C., then compounded with 15 g 35% $N_2H_4$ solution as well as 6.6 g NaOH, and agitated a further 2 hours at 120° C. Thereafter, the solution was transferred into a glass container with KPG agitator and reflux cooler and compounded with 119.6 g (190 mmoles) $N((CH_2)_3Si(OC_2H_5)_3)_3$ and a further 120 ml water and cooled down to 65° C. The mixture was agitated further at this temperature until the start of gelling. Immediately after the start of gelling, 750 ml octanal were added and after a further 6 min. 800 ml water were added. The mixture was agitated one half hour more at reflux temperature at 500 rpms and then the entire suspension was transferred into an autoclave. After a 24 hour posttreatment at 150° C., the solid was extracted twice with 1 liter ethanol each time and twice with 1 liter water each time and then dried 24 hours at 120° C. as well as 100 mbars pressure. 226.0 g (99.7 % of theoretical) polymer complex were obtained consisting of polymer units of the formula $Pt((C_6H_5)_2P-(CH_2)_3SiO_{3/2}\cdot 0.5N((CH_2)_3SiO_{3/2})_3\cdot 2SiO_2)_4$.

95% of the product present in the form of spheres exhibited a particle diameter of 0.1–1.8 mm.

Bulk density: 230 g/l

| Elementary analyses: | % Pt | % Cl | % P | % N | % Si |
|---|---|---|---|---|---|
| Theory: | 8.2 | 0 | 5.2 | 1.2 | 21.2 |
| Observed: | 7.9 | 0.05 | 4.9 | 1.1 | 22.0 |

Example 11

13.5 g (50 mmoles) $FeCl_3\ 3H_2O$ and 67.9 g (150 mmoles)

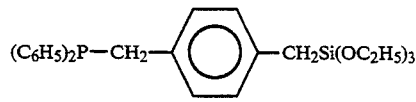

were dissolved in 500 ml ethanol. The solution was agitated one hour under reflux, then compounded with 377.9 g (750 mmoles) $N((CH_2)_3Si(OCH_3)_3)_3$ and 140 ml $H_2O$. The mixture was agitated further under reflux until the start of gelling. Immediately after the gelling, 1000 ml 2-ethylhexanol were added and, after one more minute of homogenizing, 10.6 g (50 mmoles) $(H_5C_2)Ti(OC_2H_5)_3$ as well as 1000 ml water were added. The 2-phase system was agitated 2 hours further under reflux, then cooled down, the liquid phase removed by suction and the remaining solid extracted three times with 1 liter ethanol per time. After an 8 hour drying at 100° C. and a 12 hour drying at 130° C. as well as a 12 hour drying at 160° C. under an atmosphere of $N_2$, 285 g (99.4 % of theoretical) formed polymer product were obtained consisting of units of the formula

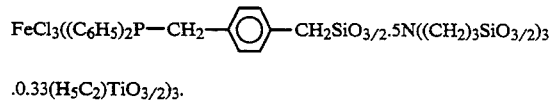

$.0.33(H_5C_2)TiO_{3/2})_3$.

Sphere size ($d_{95\%}$): 0.3–2.0 mm
Bulk density: 410 g/l

| Elementary analyses: | % Fe | % P | % N | % Ti |
|---|---|---|---|---|
| Theory: | 1.0 | 1.6 | 3.7 | 0.8 |
| Observed: | 0.9 | 1.5 | 3.6 | 0.8 |

Example 12

Starting with 12.5 g (50 mmoles) $Co(O_2CCH_3)_2\ 4H_2O$, 48.1 g (150 mmoles) $(C_6H_5)_2P-CH_2-Si(OCH_3)_3$ and 377 g (750 mmoles) $N((CH_2)_3Si(OCH_3)_3)_3$ as well as 7.4 g ( 30 mmoles ) $Al(OC_4H_9)_3$ and using the same solvent and amounts of solvent and the same method as in example 11, 268 g polymer complex were obtained consisting of polymer units of the formula $Co(O_2CCH_3)_2((C_6H_5)_2P-CH_2-SiO_{3/2}\cdot 5N((CH_2)_3SiO_{3/2})_3\cdot 0.2AlO_{3/2})_3$.

Sphere size ($d_{98\%}$): 0.2–2.0 mm
Bulk density: 360 g/l

| Elementary analyses: | % Co | % P | % N | % Al |
|---|---|---|---|---|
| Theory: | 1.1 | 1.7 | 3.9 | 0.3 |
| Observed: | 1.0 | 1.8 | 3.9 | 0.2 |

Example 13

Starting with 13.1 g (50 mmoles) NiSO₄·6H₂O, 19.5 g (50 mmoles) (C₆H₅)₂P—(CH₂)₃Si(OC₂H₅)₃ and 630.06 g (1.0 mmole) N((CH₂)₃Si(OC₂H₅)₃)₃ as well as 19.2 g (50 mmoles) Zr(OC₄H₉)₄ and using diisopropyl ether instead of 2-ethylhexanol and using the same method as in example 11, 321.0 g polymer complex were obtained consisting of units of the formula

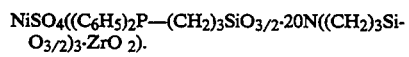

NiSO₄((C₆H₅)₂P—(CH₂)₃SiO₃/₂·20N((CH₂)₃Si-O₃/₂)₃·ZrO₂).

Sphere size (d₉₈%): 0.2–1.8 mm
Bulk density: 500 g/l

| Elementary analyses: | % Ni | % P  | % N | % Zr |
|----------------------|------|------|-----|------|
| Theory:              | 0.9  | 0.48 | 4.3 | 1.4  |
| Observed:            | 0.8  | 0.50 | 4.0 | 1.3  |

Pore volume: 0.5 ml/g (exclusively pores with a diameter less than 2 nm)

Example 14

Starting with 3.0 g (10 mmoles) OsCl₃, 217.3 g (500 mmoles) (C₆H₅)₂P—(CH₂)₃Si(OCH₃)₃ as well as 251.9 g (500 mmoles) N((CH₂)₃Si(OCH₃)₃)₃ and using 1-hexanol instead of 2-ethylhexanol as well as using methanol instead of ethanol and using the same method as in example 11 but eliminating the addition of cross-linking agent, 288.0 g polymer complex were obtained consisting of units of the formula

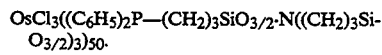

OsCl₃((C₆H₅)₂P—(CH₂)₃SiO₃/₂·N((CH₂)₃Si-O₃/₂)₃)₅₀.

Sphere size (d₉₈%): 0.2–1.6 mm
Bulk density: 360 g/l

| Elementary analyses: | % Os | % P | % N | % Si |
|----------------------|------|-----|-----|------|
| Theory:              | 0.65 | 5.3 | 2.4 | 19.3 |
| Observed:            | 0.6  | 5.1 | 2.2 | 18.6 |

Example 15

The batch for producing the polymer complex

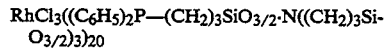

RhCl₃((C₆H₅)₂P—(CH₂)₃SiO₃/₂·N((CH₂)₃Si-O₃/₂)₃)₂₀ according to example 2 was repeated. After the conclusion of the reflux phase and the obtention of the xylene-moist, formed raw product, the 2-phase system was transferred as in example 2 into a 3 liter pressure container. At first, 50 bars CO and then 30 bars H₂ were introduced into the pressure container. The mixture was then heated under agitation to 140° C. and maintained at this temperature for 30 hours. Then it was cooled down, the pressure removed and it was worked up as in example 2. After drying, tile product was washed with 3 liters NaOH solution (pH 12) and with 2 liters water and redried 12 hours at 120° C. 58.0 g of a formed, polymeric rhodium complex catalyst were obtained consisting of polymer units of the formula

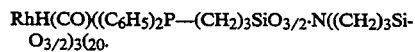

RhH(CO)((C₆H₅)₂P—(CH₂)₃SiO₃/₂·N((CH₂)₃Si-O₃/₂)₃)₂₀.

Sphere size (d₉₆%): 0.3–1.8 mm
Specific pore volume: 1.8 ml/g
Bulk density: 320 g/l

| Elementary analyses: | % Rh | % Cl | % P | % N |
|----------------------|------|------|-----|-----|
| Theory:              | 0.88 | 0    | 5.3 | 2.4 |
| Observed:            | 0.8  | 0.15 | 5.2 | 2.3 |

IR spectrum: Co approximately 1960 cm⁻¹ H approximately 2050 cm⁻¹

Example 16

50 ml of the Rh-containing polymer complex prepared in example 1 with a particle size of 0.3 to 1.2 mm were filled into a tubular reactor with an inside diameter of 16 mm. The tubular reactor was built into a continuous hydroformylation apparatus. After the system had been started tap and constant conditions had been adjusted after 48 hours of operation, the hydroformylation of hexene-1 was carried out under the following conditions:

Total pressure 120 bars
H₂/CO ratio 1:1
Temperature in the reactor 100° C.
Volumetric rate of flow octene-150 ml/h
Gas flow H₂/CO 100 Nl/h A gas-chromatic analysis (GC analysis) of the product which had been discharged and relieved of pressure yielded a composition of 98.6 % total aldehyde content (remainder: olefine isomers, octane) at an n:i product ratio of 2. The Rh content of the product was less than 0.05 ppm. After 200, 400 and 600 hours of operation, GC analyses of the product were again performed. Approximately the same composition resulted thereby and the rhodium content was approximately 30 ppb.

Example 17

5.0 g of the Pd-containing polymer complex prepared in example 4 with a particle size of 0.2–0.4 mm were combined with 234 g vinyl cyclohexene in a 1 liter autoclave. A constant pressure of 5 bars H₂ was maintained in the autoclave and the hydrogen consumed was continuously replenished from a reservoir. The mixture was then heated under agitation (1000 rpms) to 60° C. and agitated further (approximately 3 hours) until the theoretical amount of hydrogen required for the hydrogenation of a double bond had been consumed. The mixture was then cooled down and a GC analysis of the product mixture performed. According to this analysis, approximately 88 % of the educt amount used had been hydrogenated to ethylcyclohexene.

Example 18

5.0 g of the It-containing polymer complex prepared in example 7 with a particle size of 50 μm to 0.1 mm were combined with 166.2 g tetrahydrobenzaldehyde in a 1 liter autoclave. The autoclave was loaded with 10 bars hydrogen and the consumed hydrogen was continuously replenished from a reservoir. The mixture was heated under agitation (1000 rpms) to 70° C. and agitated further (approximately 4 hours) until the theoretical amount of hydrogen required for the hydrogenation of a double bond had been consumed. A GC analysis of the product obtained showed that 90% of the educt used had been converted to tetrahydrobenzyl alcohol.

Example 19

5 g of the Pt-containing polymer complex prepared in example 10 with a particle size of 0.2–0.6 mm were combined with 221.5 g octene-1 and 267.3 g $HSiCl_3$ in a 1 liter glass autoclave. The reaction mixture was heated under agitation (1000 rpms) to 100° C. and maintained at this temperature for 20 hours. A GC analysis of the product obtained showed that 95% of the octene-1 used had been converted to octyltrichlorosilane.

Further variations and modifications of the invention will become apparent to those skilled in the art from the foregoing and are intended to be encompassed by the claims appended hereto.

What is claimed:

1. A formed spherical, polymeric complex compound comprising at least one member selected from the metal containing group consisting of iron, cobalt, nickel, ruthenium, rhodium, palladium, osmium, iridium and platinum compounds; and a ligand which comprises a formed organosiloxane copolycondensate of units of the formula

 (I)

and of units of the formula

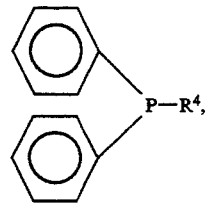 (II)

wherein the central metal atom is coordinately bound via the phosphorus atoms of the phosphine units (II) and optionally via the nitrogen atoms of the amine units (I), $R^2$ and $R^4$ are the same or different and represent a group of the formula

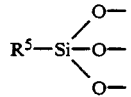 (III)

in which $R^5$ is bound directly to said phosphorus atom or to said nitrogen atom and represents a linear or branched alkylene group with 1 to 10 C atoms, a cycloalkylene group with 5 to 8 C atoms, or a unit of the formula

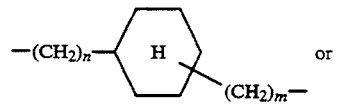 or

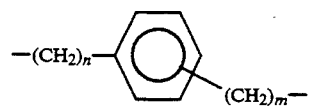

in which n and m are a number from 0 to 6, said n indicates the number of methylene groups bound to the N position or bound to the P position and m the number of methylene groups in Si position, $R^1$ represents a group selected from the group consisting of formula (III), H, $CH_3$, $C_2H_5$, and $C_3H_7$, wherein the free valences of said oxygen atoms bound to said Si atom are saturated by silicon atoms of further groups of formula (III) and/or via the metal atoms in one or several cross-linking bridge members

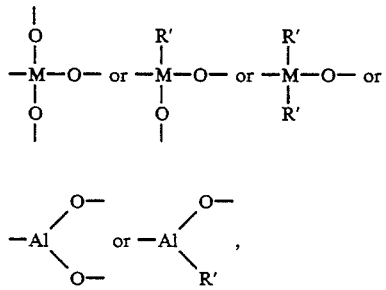 (IV)

where M is an Si, Ti or Zr atom and R' is a linear or branched alkyl group with 1 to 5 C atoms or a phenyl group, and the ratio of said silicon atoms from the groups of formula (III) to said metal atoms in the cross-linking bridge members (IV) is 1 : 0 to 1 : 20 and the molar ratio of phosphine units (II) to complexed metal units is 1 : 1 to 1000 : 1, and wherein said polymeric complex catalysts are spherical particles with a diameter of 0.01 to 3.0 mm, a BET specific surface of >0 to 1000 m²/g a specific pore volume of 0.01 to 6.5 ml/g, and a bulk density of 50 to 1000 g/l;

said complex compound produced by a method comprising:

(a) reacting in a solvent or a solvent mixture, optionally at elevated temperature, for a period of 1 minute to 48 hours, at least one member of the metal containing group consisting of hydrous or anhydrous metal compounds $FeX_3$, $FeX_2$, $CoX_3$, $CoX_2$, $NiX_2$, $RuX_3$, $RuX_3(Ch_3CN)_3$, $RuX_3(C_6H_5CN)_3$, $M_3RhX_6$, $RhX_3$, $RhX_3$, $(Ch_3CN)_3$, $RhX_3(C_6H_5CN)_3$, $RhX_2$, $RhX$, $(RhX(diene))_2$, $M_2PdX_6$, $M_2PdX_4$, $PdX_2$, $OsX_3$, $OsX_3(Ch_3CN)_3$, $OsX_2(C_6H_5CN)_3$, $M_3IrX_6$, $IrX_3$, $IrX_3(CH_3CN)_3$, $IrX_3(C_6H_5CN)_3$, $(IrX(diene))_2$, $M_2PtX_6$, $M_2PtX_4$, and $PtX_2$, in which X is selected from the group consisting of Cl, Br, I, acetyl acetonate, acetate, ½ $SO_4$, $NO_3$, and CN, and diene is selected from the group consisting of cyclooctadiene and norbornadiene, and M is selected from the group consisting of H, Na, K, and $NH_4$, with a phosphine of the formula

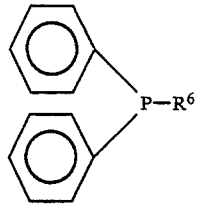 (VIII)

in which $R^6$ represents a group of the formula $$R^5—Si(OR^7)_3 \quad (IX),$$

where $R^5$ is a linear or branched alkylene group with 1 to 10 C atoms, a cycloalkylene group with 5 to 8 C atoms or a unit of the formula

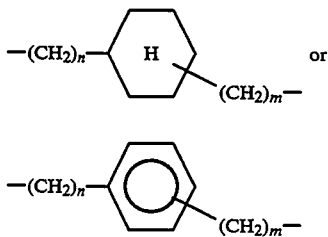

where $R^7$ is a linear or branched alkyl group with 1 to 5 C atoms, to form a metal complex, wherein the ratio between the number of moles of phosphine of formula (VIII) and the number of moles of the totally complexly bound metal atoms in said metal compounds is at least 1 : 1 to 1000 : 1, (b) adding to the product of step (a) an amino silane of the general formula

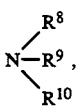 (X)

in which $R^8$ stands for H, $CH_3$, $C_2H_5$, $C_3H_7$ or a group of formula (IX) and $R^9$ and $R^{10}$ also stand for a group of formula (IX) in which $R^5$ and $R^7$ have the same range of meaning as in formula (IX), and optionally one or several compounds of the formula $$M(OR)_{2-4}R'_{0-2} \text{ or } M(OR)_{2-3}R'_{0-1} \quad (XI),$$

in which M is an Si, Ti, Zr or Al atom, R' is a linear or branched alkyl group with 1 to 5 C atoms or a phenyl group, R signifies a linear or branched alkyl group with 1 to 5 C atoms, and the ratio of the silicon atoms from the groups of formula (IX) to the metal atoms in the cross-linking agents (IX) is 1 : 0 to 1 : 20;

(c) adding to the product of step (b) an amount of water under agitation which suffices at least for a complete hydrolysis and condensation, and hydrolyzing the resulting reaction mixture for a period of time up to 6 hours;

(d) allowing the product of step (c) to gel under further agitation at a temperature in the range of room temperature to 200° C., wherein at the start of said gelling or up to one hour thereafter the product of step (c) is compounded with 10 to 2000% by weight, relative to the entire amount of said phosphine (VIII), aminoorganosilane (X) and optionally cross-linking agent (XI), of a solvent which is non-water-soluble but which dissolves the product of step (c), which has gelled or started to gel, in order to form a homogenizate;

(e) adding, immediately or in a time period of up to 10 hours, 100 to 2000% by weight of water, relative to the total amount of phosphine (VIII), aminoorganosilane (X) and optionally cross-linking agent (XI), to the viscous homogenizate of step (d), optionally with elevation of the originally adjusted temperature, whereby the organic phase containing the monomeric metal complex is dispersed in the liquid two-phase system and a solid in the shape of spheres is formed;

(f) separating the solid formed in step (d) from the liquid phase after a reaction time sufficient for this purpose at a temperature of room temperature of 200° C.;

(g) extracting the solid from step (f), optionally with a low-boiling solvent;

(h) drying the solid from step (g) at room temperature to 250° C., optionally under protective gas or in a vacuum; and (i) tempering the solid from step (h) for 1 to 100 hours at temperatures of 150° C. to 300° C. and/or classifying said solid from step (h).

2. The formed spherical, polymeric complex compound according to claim 1, wherein said molar ratio of phosphine units (II) to complexed metal units is 1 : 1, to 100 : 1.

3. The formed spherical, polymeric complex compound according to claim 1, wherein said spherical particles have a diameter of 0.05 to 2.0 mm.

4. The formed spherical, polymeric complex compound according to claim 1, wherein said specific surface is $>0$ to 700 $m^2/g$.

5. The formed spherical, polymeric complex compound according to claim 1, wherein said bulk density is 100 to 700 g/l.

6. The formed spherical, polymeric complex compound according to claim 1, wherein the ratio of units of formula (I) to units of formula (II) is 10 : 90 to 95 : 5 mole %.

7. The formed spherical, polymeric complex compound according to claim 1, wherein $R^1$ to $R^4$ are a group of the formula (III) and are identical or different.

8. The formed spherical, polymeric complex compound according to claim 1, wherein said formed copolycondensates are statistical copolycondensates, block copolycondensates, or mixed copolycondensates.

9. The formed spherical, polymeric complex compound according to claim 1, wherein $R^1$ to $R^4$ stand for a group of the formula

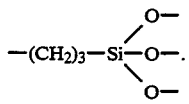 (V)

10. The formed spherical, polymeric complex compound according to claim 1, wherein said metal containing group is at least one member selected from the group consisting of metal units $FeX_3$, $FeX_2$, $CoX_3$, $CoX_2$, $NiX_2$, $RuX_3$, $RuX_2$, $RhX_3$, $RhX_2$, $RhX$, $Rh(diene)X$, $RhX(CO)$, $PdX_4$, $PdX_2$, $Pd^0$, $OsX_3$, $IrX_3$, $IrX$, $Ir(diene)X$, $IrX(CO)$, $PtX_4$, $PtX_2$, and $Pt^0$, in which X is selected from the group consisting of Cl, Br, I, H, 0.5 $SO_4$, acetylacetonate, acetate, $NO_3$, and CN, and diene is selected from the group consisting of cyclooctadiene and norbornadiene.

11. The formed spherical, polymeric complex compound according to claim 10, wherein said polymeric complex compound is selected from the group consisting of $FeX_3L_3$, $FeX_2L_4$, $CoX_3L_2$, $CoX_3L_3$, $CoX_2L_3$, $CoX_2L_4$, $NiX_2L_2$, $NiL_4$, $RuX_3L_3$, $RhX_3L_3$, $RhX_2L_3$, $RhXL_3$, $RhL_4^+X^-$, $PdX_4L_2$, $PdX_2L_2$, $PdL_4$, $OsX_3L_3$, $IrX_3L_3$, $IrXL_3$, $PtX_4L_2$, $PtX_2L_2$, and $PtL_4$, in which X is selected from the group consisting of Cl, Br, I , H, 0.5 $SO_4$, acetylacetonate, acetate, $NO_3$, and CN, and L is said ligand.

12. The formed spherical, polymeric complex compound according to claim 10, wherein said metal units are each bound to at least one phosphine unit of formula (II).

13. The formed spherical, polymeric complex compounds according to claim 12, wherein said metal units are bound only to phosphine units of formula (II).

14. The formed spherical, polymeric complex compound according to claim 10, wherein the metal content is at least 0.01% by weight and at most 20 % by weight.

15. The formed spherical, polymeric complex compound according to claim 14, wherein the metal content is 0.1 % by weight to 10 % by weight.

16. The formed spherical, polymeric complex compound according to claim 10, wherein the stoichiometric ratio between said ligands containing formula (II) and said metal is at least 1 : 1 .

17. The formed spherical, polymeric complex compound according to claim 1, wherein the stoichiometric ratio between said ligands containing formula (II) and said metals Fe, Co, Rh, Pd, Pt, or Ni is a maximum of 4 : 1 and where in the stoichiometric ratio between said ligands containing formula (II) and said metals Ru, Os, or Ir is a maximum of 3 : 1 and further comprising other ligands containing formula (I).

18. The formed spherical, polymeric complex compound according to claim 16, wherein the stoichiometric ratio between the ligands according to formula (II) and said metal is 1 : 1 and amine units of formula I are also utilized as ligands.

19. The formed spherical, polymeric complex compound according to claim 1, wherein the stoichiometric ratio between said ligands containing formula (II) and said metals Fe, Co, Rh, Pd, Pt, or Ni is above 4 : 1 and wherein the stoichiometric ratio between said ligands containing formula (II) and said metals Ru, Os, or Ir is above 3 : 1.

20. The formed spherical, polymeric complex compounds according to claim 10, further comprising other excess, non-complexing ligands according to formulas (I) and/or (II).

21. The formed spherical, polymeric complex compounds according to claim 1, wherein the thermal stability of said complex compounds is more than 130° C. in air and more than 200° C. under a atmosphere of inert gas.

* * * * *